(12) United States Patent
Childress et al.

(10) Patent No.: US 7,825,243 B2
(45) Date of Patent: Nov. 2, 2010

(54) PROCESS FOR THE PRODUCTION OF ISOCYANATOSILANE AND SILYLISOCYANURATE

(75) Inventors: R. Shawn Childress, Marietta, OH (US); Patrick J. Burns, Parkersburg, WV (US)

(73) Assignee: Momentive Performance Materials Inc., Albany, NY (US)

( * ) Notice: Subject to any disclaimer, the term of this patent is extended or adjusted under 35 U.S.C. 154(b) by 488 days.

(21) Appl. No.: 11/144,464

(22) Filed: Jun. 3, 2005

(65) Prior Publication Data

US 2006/0276644 A1 Dec. 7, 2006

(51) Int. Cl.
*C07D 251/32* (2006.01)
*C07D 251/34* (2006.01)

(52) U.S. Cl. ..................................................... 544/193
(58) Field of Classification Search ................... 544/193
See application file for complete search history.

(56) References Cited

U.S. PATENT DOCUMENTS

| | | | |
|---|---|---|---|
| 3,494,951 A | 2/1970 | Berger | |
| 3,598,852 A | 8/1971 | Berger | |
| 3,607,901 A | 9/1971 | Berger | |
| 4,064,151 A | 12/1977 | Hedaya et al. | |
| 4,540,781 A * | 9/1985 | Barsa | ............ 544/193 |
| 4,654,428 A | 3/1987 | Kurashima et al. | |
| 4,697,009 A | 9/1987 | Deschler et al. | |
| 4,880,927 A | 11/1989 | Takago et al. | |
| 5,218,133 A | 6/1993 | Pepe et al. | |
| 5,393,910 A | 2/1995 | Mui et al. | |
| 6,008,396 A | 12/1999 | Sheridan et al. | |
| 6,388,117 B2 | 5/2002 | Pinske | |
| 2004/0049064 A1 | 3/2004 | Kammel et al. | |
| 2004/0249179 A1 | 12/2004 | Kornek | |

FOREIGN PATENT DOCUMENTS

| | | |
|---|---|---|
| DE | 10108543 | 4/2002 |
| DE | 10161272 | 7/2002 |
| JP | 09208589 | 8/1997 |
| JP | 09328489 | 12/1997 |

* cited by examiner

*Primary Examiner*—Venkataraman Balasubramanian
(74) *Attorney, Agent, or Firm*—Dominick G. Vicari; Joseph S. Ostroff

(57) ABSTRACT

A process is provided for the production of isocyanatosilane from silylorganocarbamate in a cracking zone with a predetermined portion of purged reaction medium undergoing conversion in a trimerization zone to silylisocyanurate.

18 Claims, 1 Drawing Sheet

PROCESS FOR THE PRODUCTION OF ISOCYANATOSILANE AND SILYLISOCYANURATE

BACKGROUND OF THE INVENTION

This invention relates to processes for making isocyanatosilanes and 1,3,5-tris[(trialkoxysilyl)alkyl]isocyanurates.

A variety of processes are known for making isocyanatosilanes.

U.S. Pat. Nos. 3,494,951 and 3,607,901 describe processes for making isocyanatosilanes by the pyrolysis (cracking) of silylorganocarbamates.

According to the process described in U.S. Pat. No. 5,393,910, silylorganocarbamate is vaporized in a reaction zone at elevated temperature, e.g., between 300° C. and 600° C., to form an isocyanatosilane.

U.S. Pat. No. 6,008,396 discloses the so-called "hot oil" process for making isocyanatosilanes. In accordance with this process, a carbamatoorganosilane (i.e., a silylorganocarbamate) is added to an inert liquid medium and the mixture thus formed is held at a temperature and pressure effective to convert the carbamatoorganosilane to isocyanatosilane.

U.S. Pat. No. 6,388,117 describes a process of catalytically cleaving (cracking) a carbamatoorganosilane (i.e., a silylorganocarbamate) in the liquid phase to provide isocyanatosilane employing a cleavage and distillation reactor. A portion of the reaction medium, e.g., 15-25 weight percent, is purged from the bottom of the reactor in order to keep high molecular weight components at a constant level. The purged material is then allowed to mix with alcohol to quench the isocyanatosilane, is redistilled and a portion thereof is reintroduced to the reactor.

High temperature vapor phase processes for making isocyanatosilanes are described in U.S. Pat. No. 5,393,910 and U.S. Patent Application Publication Nos. 2004/0049064 and 2004/0249179. These processes suffer from the requirement for specialized equipment capable of high temperature operation with their concomitantly high capital investment requirements.

DE 10161272 describes a process wherein a silylorganocarbamate is cracked in the presence of a high molecular weight isocyanate and transition metal catalyst.

JP 09328489 describes a process where 3-aminopropylsilane is first reacted with isocyanate such as MDI to provide the corresponding urea which is then thermally cracked in the presence of catalyst to provide isocyanatosilane.

A number of processes for making isocyanatosilanes utilize low temperature cracking of a carbamate derivative.

U.S. Pat. No. 4,697,009 describes a process for making isocyanatosilane wherein an acyl-urea group is utilized as the leaving group rather than alkyl alcohols which are most common. This process suffers from the intermediate preparation that involves difficult separation of solvent and the resulting salt.

U.S. Pat. No. 4,064,151 discloses the preparation of isocyanatosilane by preparing a halosilyl carbamate by direct reaction of aminosilane in the presence of carbon dioxide and halosilyl compounds and a tertiary amine acid scavenger. The resulting halosilyl carbamate decomposes at a relatively low temperature to yield the isocyanatosilane. A difficult workup is required to obtain the product.

DE 10,108,543 describes a process where silylorganocarbamate is reacted directly with methyl trichlorosilane to provide N-silylated carbamate which then decomposes under slight heating to provide isocyanatosilane and an equimolar amount of alkoxychloromethylsilane. This method suffers from the requirement of an acid trap such as triethylamine which then requires separation and disposal or recycle.

Typical of non-cracking methods for making isocyanatosilanes are those described in JP 09208589 and U.S. Pat. No. 4,654,428 in which an aminopropylsilane is directly reacted with highly toxic phosgene to yield the desired isocyanate.

There are a number of known processes for making silylisocyanurates.

U.S. Pat. No. 3,598,852 describes a process for making silylisocyanurate in which a haloorganosilane intermediate is reacted with a metal cyanate in the presence of a high boiling polar solvent such as dimethylformamide. Subsequently, the polar solvent is removed by vacuum stripping. However, the solvent is toxic and difficult to remove.

U.S. Pat. No. 4,880,927 describes a process for preparing silylisocyanurate in which the silylisocyanate is thermally treated or heated for cyclization to the trimer in the presence of a strongly basic catalyst such as an alkali metal hydroxide or alkoxide. However, when this process is employed for the preparation of silylisocyanurate, it requires the isolation of toxic isocyanate and results in a highly colored product.

U.S. Pat. No. 5,218,133 describes the cracking of silylorganocarbamate in the presence of cracking catalyst under moderate heating and subatmospheric pressure to a non-isolated isocyanatosilane intermediate and by-product alcohol, the isocyanatosilane then undergoing trimerization in the presence of trimerization catalyst in situ to provide silylisocyanurate. Typical cracking catalysts for this process include aluminum, titanium, magnesium and zirconium alkoxides such as aluminum triethoxide which is indicated to be preferred and tin carboxylates such as dibutyltin dilaurate, dibutyltin diacetate and stannous octoate which are indicated to be preferred. Trimerization catalysts employed in the process of U.S. Pat. No. 5,218,133 include sodium methoxide and the alkali metal salts of organic acids such as the sodium, potassium, lithium and cesium salts of glacial acetic acid, propionic acid, butyric acid, hexanoic acid, and the like. Both the cracking catalyst and the trimerization catalyst are present throughout the conversion of the silylorganocarbamate to silylisocyanurate in the process of U.S. Pat. No. 5,218,133. Due to toxicity and/or environmental considerations, the foregoing aluminum-containing and tin-containing cracking catalysts, if solid, must be separated from the liquid product stream or, if liquid, will remain dissolved in the product stream where they can cause instabilities such as an increase in color and/or adversely affect the end use(s) of the product silylisocyanurate.

SUMMARY OF THE INVENTION

In accordance with the present invention, a process for the production of isocyanatosilane and silylisocyanurate is provided which comprises:

a) providing a cracking reaction medium comprising silylorganocarbamate and, optionally, a catalytically effective amount of cracking catalyst, in a cracking reaction zone;

b) subjecting the cracking reaction medium in the cracking reaction zone to cracking reaction conditions to provide isocyanatosilane and by-product alkanol;

c) recovering isocyanatosilane and by-product alkanol from the cracking reaction zone;

d) purging a portion of the cracking reaction medium during and/or following the cracking reaction;

e) introducing purged cracking-reaction medium to a trimerization reaction zone; and, f) subjecting the purged cracking reaction medium in the trimerization reaction zone to trimerization reaction conditions to provide silyisocyanurate and by-product alkanol.

Purging step (d) serves several important purposes: (1) it maintains the cracking reaction medium in the cracking reaction zone under steady-state conditions, (2) it removes impurities that might otherwise accumulate in the cracking reaction zone over time and have a detrimental effect on the reaction kinetics and/or rates, (3) it stabilizes the product isocyanatosilane in the presence of detrimental impurities that may distill overhead due to degrading reaction conditions and (4) it provides feedstocks for the production of silylisocyanurate from a common silylorganocarbamate feedstock.

The process of the invention can provide a near quantitative yield of isocyanatosilane and silylisocyanurate, both of which are industrially important products, thereby greatly reducing or eliminating the wastes associated with known processes for making these products.

DETAILED DESCRIPTION OF THE INVENTION

Figure 1:
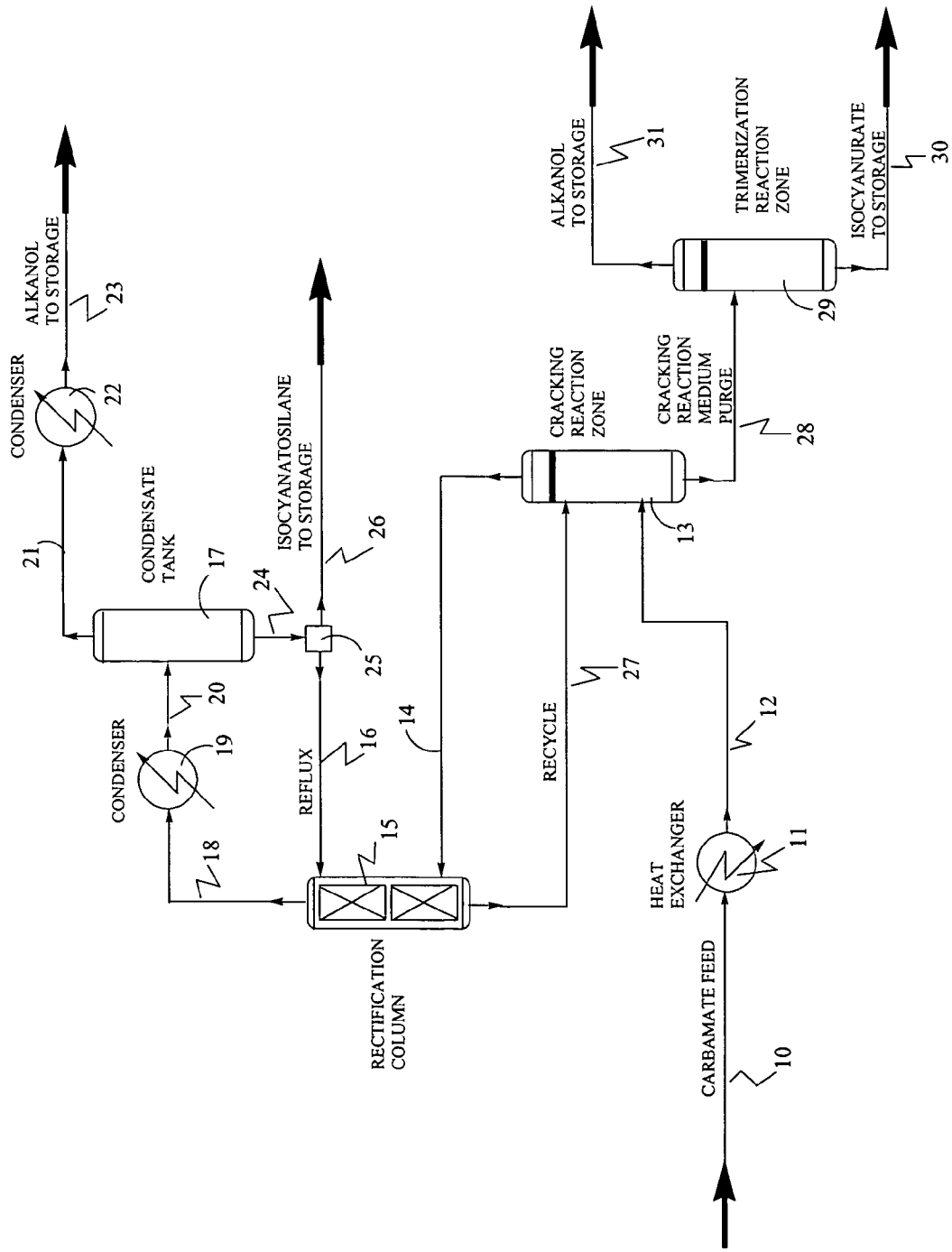
FIG. 1 is a process flow diagram illustrating the process of the invention for the concurrent production of isocyanatosilane in a cracking reaction zone and silylisocyanurate in a trimerization reaction zone.

In the cracking step of the process of the invention, at least one silylorganocarbamate of the general formula $$R_a^1SiX_{(3-a)}RNHCOOR^2$$

wherein R is a divalent hydrocarbon group of from 2 to 11 carbon atoms, and preferably from 3 to 5 carbon atoms; each $R^1$ independently is an alkyl or halogenated alkyl group of from 1 to 8 carbon atoms, an aryl group of at least 6 carbon atoms or an aralkyl group of at least 7 carbon atoms; $R^2$ is an alkyl group having 1 to 8 carbon atoms; X is a hydrolyzable alkoxy group; and, a is an integer from 0 to 3, is cracked, optionally, in the presence of cracking catalyst, under cracking reaction conditions to provide isocyanatosilane of the general formula $$R_a^1SiX_{(3-a)}RNCO$$

and by-product alkanol of the general formula $$R^2OH$$

in which R, $R^1$, $R^2$ and X have the aforestated meanings.

The silylorganocarbamate from which the foregoing isocyanatosilane is obtained can be prepared in accordance with any known or conventional process, e.g., the processes of U.S. Pat. Nos. 5,218,133 and 6,673,954, the entire contents of which are incorporated by reference herein. In brief, the silylorganocarbamate can be prepared by reacting an aminosilane, e.g., an aminoalkyltriethoxysilane such as aminopropyltrimethoxysilane, aminopropyltriethoxysilane, etc., with a dialkylcarbonate, diarylcarbonate or mixture thereof such as dimethylcarbonate, diethylcarbonate, dipropylcarbonate, dibutylcarbonate, diphenylcarbonate, etc., in the presence of a basic catalyst, e.g., an alkali metal alkoxide such as sodium methoxide (sodium methylate) which, following the reaction to produce the silylorganocarbamate, is neutralized with a carboxylic acid such as formic acid, glacial acetic acid, propanoic acid, butanoic acid, etc. to form the corresponding alkali metal carboxylate, i.e., a carboxylate salt which is useful as a catalyst for the cracking reaction of the process of this invention.

When conducting the cracking operation of this invention in the presence of cracking catalyst, it is advantageous to employ a silylorganocarbamate in the process of this invention which is made with an alkali metal alkoxide subsequently neutralized with carboxylic acid since the cracking catalyst for this operation will then already be present in the silylorganocarbamate reactant. Accordingly, it is a particular aspect of this invention to prepare a silylorganocarbamate in this way for utilization in the cracking step of the process herein. Preparing the silylorganocarbamate reactant in the aforesaid manner obviates the need to remove alkali metal carboxylate salt therefrom which is indicated to be preferred in U.S. Pat. No. 5,218,133. If desired, salt present in the silylorganocarbamate can be removed therefrom by known methods such as filtration and/or distillation. Removal of a portion of the salt is advantageous in the cracking zone because the salt acts as a strong trimerization catalyst.

Examples of silylorganocarbamate reactant which are useful in carrying out the cracking step of the process of this invention are methyl N-3-(trimethoxysilyl)-propylcarbamate, ethyl N-3-(trimethoxysilyl)propylcarbamate, methyl N-3-(triethoxysilyl)propylcarbamate, methyl N-3-(methyldimethoxysilyl)propylcarbamate, methyl N-3-(dimethylmethoxysilyl)propylcarbamate, methyl N-3-(triethoxysilyl) propylcarbamate, ethyl N-3-(triethoxysilyl) propylcarbamate, methyl N-4-(trimethoxysilyl) butylcarbamate, methyl N-3-(triethoxysilyl)butylcarbamate, and the like.

When a cracking catalyst is employed, it may be any of those heretofore employed for this reaction, e.g., those disclosed in U.S. Pat. No. 5,218,133, the entire contents of which are incorporated by reference herein. Advantageously, the cracking catalyst is selected to be a carboxylate salt, in particular, at least one of ammonium carboxylate, alkali metal carboxylate or alkaline earth metal carboxylate.

The term "ammonium" shall be understood herein to include the ammonium cation, $NH_4^+$, and the mono-, di-, tri- and tetrahydrocarbyl-substituted variants thereof.

The term "carboxylate" shall be understood herein to mean the salt of a monocarboxylic acid, dicarboxylic acid or acid anhydride of up to about 20 carbon atoms and advantageously of up to about 12 carbon atoms.

Illustrative of the ammonium carboxylate salt cracking catalysts herein are ammonium formate, ammonium acetate, ammonium propanoate, ammonium n-butanoate, ammonium n-pentanoate, ammonium 2-methylpropanoate, ammonium 3-methylbutanoate (valerate), ammonium benzoate, tetramethylammonium acetate, tetraethylammonium acetate, tetrabutylammonium acetate, tetramethylammonium 2-ethylhexanoate, tetraethylammonium 2-ethylhexanoate, tetramethylammonium benzoate, tetraethylammonium benzoate, tetrapropylammonium benzoate, tetrabutylammonium benzoate, and the like.

Illustrative of the alkali metal carboxylates are lithium formate, lithium acetate, lithium propanoate, sodium formate, sodium acetate, sodium propanoate, sodium n-butanoate, sodium n-hexanoate, sodium oleate, sodium laurate, sodium palmitate, disodium malonate, disodium succinate, disodium adipate, and the like.

Illustrative of the alkaline earth metal carboxylate cracking catalysts herein are the calcium, magnesium and barium carboxylates derived from formic acid, acetic acid, propanoic acid, n-butanoic acid, and the like.

The alkali metal carboxylates are readily available or are easily manufactured, e.g., in situ, and generally provide good results. Alkali metal formates are especially advantageous for use herein in that they appear to be more readily removed by filtration from the reaction product mixture than, say, the corresponding acetates and carboxylates of higher carboxylic acids. The alkali metal carboxylate salt is advantageously already present in the silylorganocarbamate reactant due to the manufacturing procedure described above in which the alkali metal alkoxide catalyst used in making the silylorganocarbamate is neutralized post-reaction with carboxylic acid. Alternatively, the alkali metal carboxylate can be generated in situ by the addition of alkali metal alkoxide and carboxylic acid to the silylorganocarbamate and/or previously prepared alkali metal carboxylate can be added to the silylorganocarbamate.

Regardless of how the optional carboxylate salt catalyst is introduced into the reaction medium, when utilized herein it will be present in a catalytically effective amount for the cracking reaction. With transfer of a portion of the cracking reaction medium to the trimerization zone, the optional carboxylate salt catalyst will also be present for the trimerization reaction to provide product silylisocyanurate. In general, from about 0.01 to about 1 weight percent, and advantageously from about 0.05 to about 0.2 weight percent, of carboxylate salt catalyst based upon the total amount of silylorganocarbamate in the liquid cracking reaction medium can be utilized with generally good results.

The cracking step of the process of the invention can be carried out by heating the silylorganocarbamate-containing reaction mixture, optionally, in the presence of carboxylate salt cracking catalyst, under suitable cracking conditions, e.g., elevated temperature and subatmospheric pressure, for a sufficient period of time for conversion of silylorganocarbamate to isocyanatosilane to take place. Gas phase or liquid phase conditions can be utilized. The conditions are advantageously those for liquid phase reaction. When the cracking reaction zone is operated under gas phase conditions, cracking reaction medium will be purged from the bottom of rectification apparatus associated with the cracking reaction zone, e.g., rectification column 15 of FIG. 1. When the cracking reaction zone is operated under liquid phase conditions, cracking reaction medium will be purged from the cracking reaction zone, i.e., cracking reaction zone 13 of FIG. 1. While an inert organic solvent or mixture of solvents can be employed, ordinarily there is little advantage to doing so.

Those skilled in the art can readily optimize the cracking conditions for a particular silylorganocarbamate reactant and, if employed, optional carboxylate salt cracking catalyst, employing straightforward experimental procedures. Residence times ranging from about 1 minute up to about 24 hours, advantageously from about 15 minutes up to about 5 hours, temperatures ranging from about 140° C. to about 500° C., advantageously from about 180° C. to about 220° C., and pressures ranging from about 5 to about 500 millimeters Hg, advantageously from about 50 to about 300 millimeters Hg, generally provide good results.

Examples of isocyanatosilane that can be produced in the cracking reaction step are 3-isocyanatopropyltrimethoxysilane, 3-isocyanatopropylmethyl-dimethoxysilane, 4-isocyanatobutyltrimethoxysilane, 4-isocyanatobutylmethyldimethoxysilane, 3-isocyanatopropyltriethoxysilane, 3-isocyanatopropylethyl-diethoxysilane, 3-isocyanatopropyldimethylmethoxysilane, 4-isocyanatobutyltriethoxysilane, 3-isocyanatopropylphenylmethylmethoxysilane, and the like.

During and/or following the aforedescribed cracking reaction step to produce isocyanatosilane, a predetermined portion of the cracking reaction medium will be continuously or intermittently purged and transferred to the trimerization zone where production of silylisocyanurate takes place. For example, from about 1 to about 70, and advantageously, from about 10 to about 50, weight percent of the cracking reaction medium based on the weight of incoming silylorganocarbamate feed can be continuously purged from the cracking reaction zone. The purged cracking reaction medium can be transferred directly to the trimerization reaction zone to there undergo conversion to silylisocyanurate or it can be temporarily stored in a holding tank or vessel so that upon completion of the cracking reaction, the stored cracking reaction medium can be reintroduced to the zone from which it was purged, now being operated as the trimerization reaction zone.

Conversion of purged cracking reaction medium in the trimerization reaction zone can be represented by the general reaction scheme:

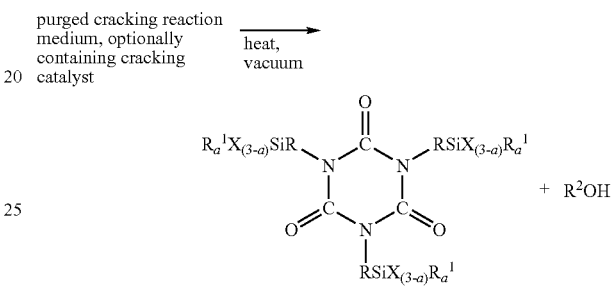

in which each R, $R^1$, X and a have the aforestated meanings.

Like the cracking reaction, the trimerization reaction can be carried out in the presence or absence of catalyst. Advantageously, when the use of catalyst for the trimerization reaction is desired, it will be the same ammonium-, alkali metal- or alkaline earth metal carboxylate catalyst optionally utilized in the cracking operation.

Among the silylisocyanurates that can be obtained in the trimerization step of the process of this invention are 1,3,5-tris(trimethoxysilylpropyl)isocyanurate, 1,3,5-tris(methyldimethoxysilylpropyl)isocyanurate, 1,3,5-tris(trimethoxysilylbutyl)isocyanurate, 1,3-5-tris (methyldimethoxysilylbutyl)isocyanurate, 1,3-5-tris (triethoxysilylpropyl)isocyanurate, 1,3,5-tris (phenylmethylmethoxysilylpropyl)isocyanurate, and the like.

The process of the invention will now be described in accordance with FIG. 1, a process flow diagram illustrating the production of isocyanatosilane in a cracking reaction zone operated under liquid phase reaction conditions and concurrent conversion of purged cracking reaction medium to silylisocyanurate in a trimerization reaction zone.

Trimerization reaction conditions can be the same as, or different from, those employed in the cracking operation and advantageously include residence times of from about 30 minutes up to about 24 hours, advantageously from about 4 up to about 10 hours, temperatures of from about 150 to about 300° C., advantageously from about 180 to about 220° C., and pressures on the order of from about 5 to about 500 millimeters Hg, advantageously from about 80 to about 300 millimeters Hg.

Silylorganocarbamate feed, optionally containing ammonium-, alkali metal- and/or alkaline earth metal carboxylate catalyst, in conduit 10 is pre-heated by passage through heat exchanger 11 and introduced via conduit 12 into the base of cracking reaction zone 13 where cracking of the silylorganocarbamate under liquid phase conditions to provide isocyanatosilane and by-product alkanol takes place. As the cracking reaction proceeds, the product isocyanatosilane, by-product alkanol and unreacted silylorganocarbamate overheads are introduced through conduit 14 into the base of rectification column 15 which is supplied via conduit 16 with reflux from condensate tank 17. The gas/liquid overheads in rectification column 15 passes via line 18 through condenser 19 to provide technical grade isocyanatosilane condensate containing a small amount of unreacted silylorganocarbamate, e.g., about 5 weight percent or less thereof, which enters condensate tank 17 via line 20. The alkanol overheads in condensate tank 17 passes therefrom via conduit 21 through condenser 22, the alkanol condensate thereafter being transferred via conduit 23 to storage. An isocyanatosilane product in condensate tank 17 is withdrawn therefrom through conduit 24 with a portion thereof being diverted by valve 25 to serve as reflux liquid for rectification column 14 with another portion thereof being transferred through line 26 to storage.

The liquid bottoms from rectification column 15 containing mainly unreacted silylorganocarbamate together with a small amount of isocyanatosilane are recycled through conduit 27 to cracking zone 13.

As isocyanatosilane is being produced in cracking zone 13, a predetermined amount of liquid cracking reaction medium is continuously purged therefrom and transferred through line 28 to trimerization reaction zone 29 where trimerization of components of the purged cracking reaction medium takes places to provide silyisocyanurate product, withdrawn to storage through conduit 30, and alkanol by-product, withdrawn to storage through conduit 31.

The following example is illustrative of the process of the invention.

Example

To a stirred cracking reactor equipped with rectification column, previously distilled methyl N-3-(trimethoxysilyl) propylcarbamate (made from 3-aminopropyltrimethoxysilane (A-1110 from GE Silicones) and dimethylcarbonate) containing no cracking catalyst was subjected to cracking conditions (200-210° C. and 50-100 mmHg). When the column profile indicated that cracking had been achieved, the N-3-(trimethoxysilyl)propylcarbamate was fed continuously from an auxiliary tank. 3-isocyanatopropyltrimethoxysilane reaction product, unreacted methyl N-3-(trimethoxysilyl) propylcarbamate and methanol by-product were then rectified to provide isocyanate of the desired purity for commercial use. Periodically, the cracking zone was purged by utilizing a bottom takeoff at the rate of approximately 10 weight percent of the incoming carbamate feed. This purge was transferred to a separate trimerization reaction zone where it was thermally trimerized as hereinafter described.

To a 2 L 4 necked round bottom flask equipped with overhead stirrer, Vigreux column, thermocouple, and distillation head was added 670 grams of the aforementioned purged cracking reaction medium which consisted of a 62 weight percent mixture of methyl N-3-(trimethoxysilyl)propylcarbamate and 3-isocyanatopropyl-trimethoxysilane and 15 weight percent of 1,3,5-tris[3-(trimethoxysilyl) propyl]-isocyanurate. This mixture was treated with approximately 1.3 mL of 25 weight percent sodium methoxide solution and approximately 3 mL of formic acid to produce sodium formate in situ. The stirred reaction mixture was then rapidly heated to 210° C. with initial pressure set at 210 mmHg. The temperature was maintained at about 210° C. for 1 hr. The pressure was gradually reduced to 90 mmHg during this period. The mixture was then cooled and filtered. The conversion, which was measured by disappearance of the combined carbamate/isocyanate peaks using gas chromatography, was found to be 89 percent. The 1,3,5-tris[3-(trimethoxysilyl)propyl]isocyanurate made up approximately 71 wt. percent of the final mixture.

While the process of the invention has been described with reference to certain embodiments, it will be understood by those skilled in the art that various changes may be made and equivalents may be substituted for elements thereof without departing from the scope of the invention. In addition, many modifications may be made to adapt a particular situation or material to the teachings of the invention without departing from the essential scope thereof. Therefore, it is intended that the invention not be limited to the particular embodiment disclosed as the best mode contemplated for carrying out the process of the invention but that the invention will include all embodiments falling within the scope of the appended claims.

What is claimed is:

1. A continuous process for the concurrent production of isocyanantosilane in a cracking reaction zone and silylisocyanurate in a trimerization zone, which comprises:

a) continuously providing a silylorganocarbamate of the general formula;

$$R_a^1 SiX_{(3-a)}RNHCOOR^2,$$

wherein R is a divalent hydrocarbon group of from 2 to 11 carbon atoms; $R^1$ is an alkyl or halogenated alkyl group of from 1 to 8 carbon atoms, an aryl group of at least 6 carbon atoms or an aralkyl group of at least 7 carbon atoms; $R^2$ is an alkyl group having 1 to 8 carbon atoms; X is a hydrolysable alkoxy group; and a is an integer from 0 to 3 to a cracking reaction medium comprising silylorganocarbamate, in the absence or, optionally, in the presence of a catalytically effective amount of cracking catalyst selected from the group consisting of ammonium carboxylate, alkali metal carboxylate and alkaline earth metal carboxylate, in a cracking reaction zone;

b) subjecting the cracking reaction medium in the cracking reaction zone to cracking reaction conditions to provide isocyanatosilane of general formula:

$$R_a^1 SiX_{(3-a)}RNCO,$$

wherein R is a divalent hydrocarbon group of 2 to 11 carbon atoms, $R^1$ is an alkyl or halogenated alkyl group of from 1 to 8 carbon atoms, an aryl group of at least 6 carbon atoms or an aralkyl group of at least 7 carbon atoms; X is a hydrolysable alkoxy group; and a is an integer from 0 to 3, and by-product alkanol of general formula:

$$R^2OH$$

wherein $R^2$ is an alkyl group having 1 to 8 carbon atoms;

c) recovering isocyanatosilane and by-product alkanol from the cracking reaction zone;

d) purging continuously a portion of the cracking reaction medium during the cracking reaction;

e) introducing purged cracking reaction medium to a trimerization reaction zone; and, f) subjecting the purged cracking reaction medium in the trimerization reaction zone to trimerization reaction conditions to provide silyisocyanurate of general formula;

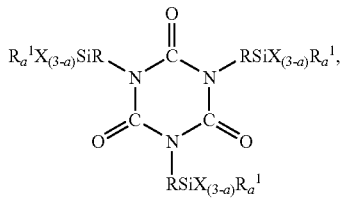

wherein R is a divalent hydrocarbon group of from 2 to 11 carbon atoms; $R^1$ is an alkyl or halogenated alkyl group of from 1 to 8 carbon atoms, an aryl group of at least 6 carbon atoms or an aralkyl group of at least 7 carbon atoms; X is a hydrolysable alkoxy group; and a is an integer from 0 to 3 and by-product alkanol of general formula:

$R^2OH$ wherein $R^2$ is an alkyl group having 1 to 8 carbon atoms.

2. The process of claim 1 wherein the cracking reaction zone is operated under liquid phase conditions.

3. The process of claim 1 wherein the silylorganocarbamate is at least one of methyl N-3-(trimethoxysilyl)-propylcarbamate, ethyl N-3-(trimethoxysilyl)propylcarbamate, methyl N-3-(triethoxysilyl)propylcarbamate, methyl N-3-(methyldimethoxysilyl)-propylcarbamate, methyl N-3-(dimethylmethoxysilyl)-propylcarbamate, methyl N-3-(triethoxysilyl) propylcarbamate, ethyl N-3-(triethoxysilyl)-propylcarbamate, methyl N-3-(methoxydiethoxysilyl) propylcarbamate, methyl N-3-(trimethoxysilyl) butylcarbamate and methyl N-3-(triethoxysilyl)-butylcarbamate, the isocyanatosilane is at least one of 3-isocyanato propyltrimethoxysilane, 3-isocyanatopropylmethyldimethoxysilane, isocyanatobutyltrimethoxysilane, isocyanatobutylmethyldimethoxysilane, 3-isocyanatopropyltriethoxysilane, isocyanatopropylethyldiethoxysilane, isocyanatopropyldimethylmethoxysilane, isocyanatopropylmethoxydiethoxysilane, isocyanatobutyltriethoxysilane and isocyanatopropylphenylmethylmethoxysilane and the silyisocyanurate is at least one of 1,3,5-tris(trimethoxysilylpropyl)isocyanurate, 1,3,5-tris(methyldimethoxysilylpropyl) isocyanurate, 1,3,5-tris(trimethoxysilylbutyl)isocyanurate, 1,3,5-tris(methyldimethoxysilylbutyl)isocyanurate, 1,3,5-tris(triethoxysilyl-propyl)isocyanurate and 1,3,5-tris(phenylmethylmethoxysilylpropyl)isocyanurate.

4. The process of claim 1 wherein the carboxylate salt is an alkali metal carboxylate salt of a carboxylic acid of from 1 to about 20 carbon atoms.

5. The process of claim 1 wherein the carboxylate salt is an alkali metal carboxylate salt of a carboxylic acid of from 1 to about 12 carbon atoms.

6. The process of claim 1 wherein the carboxylate salt is selected from the group consisting of lithium formate, sodium formate, potassium formate, lithium acetate, sodium acetate, potassium acetate, lithium propanoate, sodium propanoate, potassium propanoate, and mixtures thereof.

7. The process of claim 1 wherein the silylorganocarbamate contains alkali metal carboxylate salt and is obtained by the process which comprises reacting an aminosilane with a dialkylcarbonate in the presence of alkali metal alkoxide catalyst to provide silylorganocarbamate and neutralizing the alkali metal alkoxide with carboxylic acid to produce alkali metal carboxylate salt which remains in the silylorganocarbamate to function as cracking catalyst in the cracking reaction zone.

8. The process of claim 7 wherein the alkali metal alkoxide is at least one of sodium methoxide, sodium ethoxide, sodium propoxide, sodium tert-butoxide, potassium methoxide, potassium ethoxide, potassium propoxide or potassium tert-butoxide and the carboxylic acid is at least one of formic acid, acetic acid and propanoic acid.

9. The process of claim 7 wherein the silylorganocarbamate contains from about 0.01 to about 0.5 weight percent alkali metal carboxylate.

10. The process of claim 7 wherein the silylorganocarbamate contains from about 0.05 to about 0.2 weight percent alkali metal carboxylate.

11. The process of claim 7 wherein the alkali metal carboxylate salt is selected from the group consisting of lithium formate, sodium formate, potassium formate, lithium acetate, sodium acetate, potassium acetate, lithium propanoate, sodium propanoate, potassium propanoate, and mixtures thereof.

12. The process of claim 1 wherein the reaction conditions in the cracking reaction zone include a residence time therein of from about 1 minute to about 24 hours, a temperature of from about 140° C. to about 500° C. and a pressure of from about 5 to about 500 millimeters Hg.

13. The process of claim 1 wherein the reaction conditions in the cracking reaction zone include a residence time therein of from about 15 minutes to about 1 hour, a temperature of from about 180° C. to about 220° C. and a pressure of from about 50 to about 300 millimeters Hg.

14. The process of claim 1 wherein the reaction conditions in the trimerization zone are the same as, or different from, those employed in the cracking operation and include a residence time therein of from about 30 minutes to about 24 hours, a temperature of from about 150° C. to about 300° C. and a pressure of from about 50 to 300 millimeters Hg.

15. The process of claim 1 wherein during cracking, from about 1 to about 70 weight percent of the cracking reaction medium is purged based on the weight of the incoming silylorganocarbamate feed continuously purged from the cracking zone.

16. The process of claim 1 wherein during cracking from about 10 to about 50 weight percent of cracking reaction medium is based on the weight of the incoming silylorganocarbamate feed continuously purged from the cracking zone.

17. The process of claim 1 wherein no cracking catalyst is present in the cracking zone.

18. The process of claim 1 wherein recovering isocyanatosilane and by-product alkanol from the cracking reaction zone of step (c) through the use of a rectification column.

* * * * *